United States Patent [19]

Bryant

[11] 4,422,955

[45] Dec. 27, 1983

[54] PROCESS FOR SUBSTITUTION OF AROMATIC ORGANIC COMPOUNDS

[75] Inventor: Robert J. Bryant, Stanley, England

[73] Assignee: Sterling Drug Inc., New York, N.Y.

[21] Appl. No.: 327,714

[22] Filed: Dec. 4, 1981

[30] Foreign Application Priority Data

Dec. 17, 1980 [GB] United Kingdom ............... 8040383

[51] Int. Cl.$^3$ ........................ B01J 31/28; B01J 31/30
[52] U.S. Cl. .................................. 502/169; 546/156; 549/62; 568/337; 568/629; 502/170
[58] Field of Search ........................... 252/428, 429 R

[56] References Cited

U.S. PATENT DOCUMENTS

| 3,118,001 | 1/1964 | Riemenschneider | 252/429 R X |
| 3,609,098 | 9/1971 | Brown | 252/428 X |
| 4,102,933 | 7/1978 | Howarth et al. | 260/613 D |
| 4,218,567 | 8/1980 | Manchand et al. | 562/475 |

FOREIGN PATENT DOCUMENTS 55-94329 of 1980 Japan .
1338890 11/1973 United Kingdom .

OTHER PUBLICATIONS

Pepper et al., Can. J. Chem., 31, 476–483 (1953).
Bacon et al., Proc. Chem. Soc., 113–114 (1962).
Bacon et al., J. Chem. Soc., 1097–1119 (1964).
Bacon et al., J. Chem. Soc. C, 308–315 (1969), 1978–1981 (1969).
Hardy et al., J. Amer. Chem. Soc., 80, 1716–1718 (1958).
Newman et al., J. Org. Chem., 2525 (1961).
Adams et al., J. Amer. Chem. Soc., 81, 4927–4931 (1959).
McKillop et al., Syn. Comms., 34–43 (1974).
Litvak et al., Zh. Org. Khim., 10, 2373–2376 (1974).
Torii et al., J. Org. Chem., 44, 3305–3310 (1979).
Derwent Abstract of Japanese Patent Publication No. 127,368/80.

*Primary Examiner*—Patrick Garvin
*Attorney, Agent, or Firm*—B. Woodrow Wyatt; Paul E. Dupont; Frederik W. Stonner

[57] ABSTRACT

The invention relates to a process for substituting for a halogen atom attached to the nuclear carbon atom of an aromatic ring, a substituent of the formula —O—R wherein R represents alkyl, alkenyl, alkynyl or benzyl, which process comprises reacting the halogen-substituted aromatic compound with an alcoholate of the formula $M^{n+}[O-R]_n^-$ wherein M is an alkali metal atom or alkaline earth metal atom, n is the valency of M, and R is as defined above, in the presence of an active catalyst mixture comprising (i) a formic acid ester of an organic alcohol having the formula $R^2$—O—CO—H wherein $R^2$ is as defined for R above; and (ii) a cuprous salt; in a liquid medium which is a solvent for the catalyst mixture and in which the halogen-substituted aromatic compound is at least partially soluble, under substantially anhydrous conditions and a non-oxidizing atmosphere. The invention further relates to a catalyst used in the above process.

8 Claims, No Drawings

PROCESS FOR SUBSTITUTION OF AROMATIC ORGANIC COMPOUNDS

BACKGROUND OF THE INVENTION

1. Field of the Invention

The invention relates to processes for substitution of aromatic organic compounds. More specifically, the invention relates to processes for the introduction of alkoxy substituents or what may broadly be regarded as "alkoxy-type" substituents in replacement for halogen substituents upon an aromatic nucleus; and to catalytic materials employed therein.

2. Description of the Prior Art

The simplest of alkoxy substituents is the methoxy group, which is moreover probably the one most commonly encountered, occurring with remarkable frequency in the structures of biologically-active compounds. There are numerous existing commercial syntheses, and many more potentially-important syntheses, in which it is necessary either directly or indirectly to introduce an alkoxy substituent, usually a methoxy group, or some kind of alkoxy-type substituent into an aromatic ring system. Indirect routes by their nature tend to be economically less attractive than direct ones where an alkoxy residue substitutes directly into the aromatic ring. Such reactions have been known for some time, but activation of the ring by electron withdrawing groups such as nitro-groups was usually necessary for efficient conversion.

Copper catalysis [Pepper et al., Can. J. Chem., 31, 476-483 (1953)] was little used until the late 1950's, and such reactions, especially the Ullmann reaction, although of more general application, tended to proceed only under forcing conditions, i.e., high temperatures (180°-250° C.) and costly solvents such as quinoline or substituted pyridines, and yields were often low. Because copper powder was usually employed, reproducibility was often poor since the catalysis is in fact homogeneous and the physical state of the copper powder varied in its activity.

Work in the early 1960's [Bacon et al., Proc. Chem. Soc., 113-114 (1962); Bacon et al. J. Chem. Soc., 1097-1119 (1964)] clarified the application of copper catalysts in aromatic substitution and paved the way to a series of publications on synthetic applications. It was shown that cuprous salts were far more active catalysts, especially when solubilized by suitable solvents, especially aprotic dipolar ones such as dimethylformamide (DMF) and dimethyl sulfoxide (DMSO). These solvents lowered the temperature at which reasonable reaction rates were achieved from about 180°-200° C. to 130°-160° C. It was also shown that cuprous oxide tended to favor reduction, especially in the presence of suitable hydride donors, and in fact reduction was often a competing reaction, especially in certain solvents [Bacon et al., (1964) supra; Bacon et al., J. Chem. Soc. C, 308-315 (1969)].

By the mid-1970's, the chemistry of copper catalysed aromatic substitution could be summarized as follows. Various nucleophiles [Bacon et al., (1969) supra; Bacon et al., J. Chem. Soc. C, 1978-1981 (1969)], e.g., halides [Hardy et al., J. Amer. Chem. Soc., 80, 1716-1718 (1958)], cyanides [Newman et al., J. Org. Chem., 2525 (1961)], phenoxides [Bacon et al., (1964) supra], thiophenoxides [Adams et al., J. Amer. Chem. Soc., 81, 4927-4931 (1959)], hydroxide [British Pat. No. 1,338,890 (Nov. 28, 1973)], and alkoxides [Pepper et al., (1953) supra; U.S. Pat. No. 4,102,933 (July 25, 1978); McKillop et al., Syn. Comms., 35-43 (1974); Litvak et al., Zh. Org. Khim., 10, 2373-2376 (1974)] would displace the halide, usually bromide, in aromatic halides in the presence of catalytic quantities (20-50 molar %) of copper(I) ion salts at moderate temperatures (130°-170° C.) in high boiling bases such as α-picoline [Hardy et al., (1958) supra] and 2,4,6-collidine [Bacon et al., J. Chem. Soc., 1978-1981 (1969)], or dipolar aprotic solvents such as DMF [McKillop et al., (1974) supra], N-methylpyrrolidone [Newman et al., (1961) supra] and DMSO [Bacon et al., (1964) supra]. Yields were good but reaction times were, in general, long. In special cases these reactions were sufficiently good to be of economic interest [British Pat. No. 1,338,890].

Litvak et al., (1974) supra, Torii et al., J. Org. Chem., 44, 3305-3310 (1979) and U.S. Pat. No. 4,218,567 (Aug. 19, 1980) disclose that, in specific cases, good yields can be achieved in the copper catalyzed substitution of a methoxy substituent for aromatic bromide under somewhat milder conditions, but nevertheless still in expensive solvents (DMF, pyridine).

SUMMARY OF THE INVENTION

It has now been shown that by use of a liquid reaction medium containing copper in solution, it is possible to achieve methoxylation and, within limits, other alkoxylations, of many aromatic compounds, and indeed to do so in a clean and reproducible manner, with acceptable and usually good yields, at temperatures which are below and often far below those required using a metallic copper catalyst, indeed normally below 100° C., and at ambient or near-ambient pressures.

Accordingly, in one aspect the invention provides a process for the preparation of a compound of the general formula:

wherein A represents the residue of an aromatic ring forming the whole or a part of a monocyclic or polycyclic, at least partially-aromatic, carbocyclic and/or heterocyclic ring system, optionally bearing one or more other substituents inert to the reactants here employed, and R represents an optionally-substituted substituent selected from the group consisting of alkyl, alkenyl, alkynyl and benzyl having up to 12 carbon atoms, which process comprises causing an aromatic compound of the general formula:

wherein A is as defined above and X represents a bromine, chlorine or iodine atom, to react with an alcoholate of the general formula:

wherein M represents an alkali metal atom or an alkaline earth metal atom; n is the valency of M; and R is as defined above, in the presence of a catalytically-effective amount of an active catalyst mixture comprising:

(i) a formic acid ester of an organic alcohol, conveniently referred to as a "formate", having the general formula:

$$R^2—O—CO—H \quad (IV)$$

wherein $R^2$ represents an optionally-substituted substituent selected from the group consisting of alkyl, alkenyl, alkynyl and benzyl having up to 12 carbon atoms; and (ii) a cuprous salt;

in a liquid medium which is a solvent for the catalyst mixture and in which the compound of formula I is at least partially soluble, under substantially anhydrous conditions and a non-oxidizing atmosphere, to yield the desired corresponding aromatic organic compound of formula V.

In another aspect, the invention provides a process for substituting for a halogen atom attached to the nuclear carbon atom of an aromatic ring, wherein the halogen-substituted aromatic ring comprises the whole or part of a partially or wholly aromatic substrate selected from the group consisting of a monocyclic carbocyclic compound, a polycyclic carbocyclic compound, a monocyclic heterocyclic compound and a polycyclic heterocyclic compound; a substituent of the formula —O—R, wherein R represents a substituent selected from the group consisting of alkyl having from 1 to 12 carbon atoms, alkenyl having from 3 to 12 carbon atoms, alkynyl having from 3 to 12 carbon atoms and benzyl; which process comprises reacting said substrate with an alcoholate of the formula:

$$M^{n+}[O—R]_n^{\ominus} \quad (II)$$

wherein M represents an alkali metal atom or an alkaline earth metal atom; n is the valency of M, and R is as defined above, in the presence of a catalytically-effective amount of an active catalyst mixture comprising:

(i) a formic acid ester of an organic alcohol having the formula:

$$R^2—O—CO—H \quad (IV)$$

wherein $R^2$ represents a substituent selected from the group consisting of alkyl having from 1 to 12 carbon atoms, alkenyl having from 3 to 12 carbon atoms, alkynyl having from 3 to 12 carbon atoms and benzyl, and (ii) a cuprous salt;

in a liquid medium which is a solvent for the catalyst mixture and in which the substrate is at least partially soluble, under substantially anhydrous conditions and a non-oxidizing atmosphere.

In yet another aspect, the invention provides a catalyst for use in the above described process which comprises a mixture of a formic acid ester of an organic alcohol having the formula $$R^2—O—CO—H \quad (IV)$$

wherein $R^2$ represents a substituent selected from the group consisting of alkyl having from 1 to 12 carbon atoms, alkenyl having from 3 to 12 carbon atoms, alkynyl having from 3 to 12 carbon atoms and benzyl; and a cuprous salt; said catalyst being substantially anhydrous and protected against oxidative breakdown.

DETAILED DESCRIPTION OF THE INVENTION

As appears above, and will further appear from the examples hereinafter given, the ring system of the aromatic organic compound of general formula I used as starting material, and thus correspondingly of the aromatic organic compound of general formula V which is the desired final product of the processes of this invention, can be of the most diverse nature. Purely for purposes of illustration, and thus without any limitation upon the scope of this invention, it can be said that the organic residue of general formula:

 (VI)

wherein A has its previously-assigned meaning, may represent the residue of:

a fused polycyclic carbocyclic wholly-aromatic compound such as tetracyclic chrysene or benzanthracene, tricyclic anthracene or phenanthrene or bicyclic naphthalene etc.;

a non-fused polycyclic carbocyclic wholly-aromatic compound such as 2-, 3- or 4-phenoxybenzene etc.;

a fused polycyclic partially-heterocyclic wholly-aromatic compound such as bicyclic quinoline or indole etc.;

a non-fused polycyclic partially-heterocyclic wholly-aromatic compound such as the phenyl pyridines, and naphthyl thiophenes etc.;

a monocyclic carbocyclic wholly-aromatic compound such as benzene, toluene, etc.;

a monocyclic heterocyclic wholly-aromatic compound such as pyridine, furan, thiophene etc.;

a fused polycyclic carbocyclic partially-aromatic compound such as tetralin, fluorene, indene, etc.;

a non-fused, polycyclic, carbocyclic partially-aromatic compound such as 2-, 3- and 4-cyclohexylbenzene etc.;

a fused, polycyclic, partially-heterocyclic, partially-aromatic compound such as tetrahydroquinoline, dihydroindole etc.; or a non-fused, polycyclic, partially-heterocyclic, partially-aromatic compound such as 2-, 3- and 4-cyclohexylpyridine etc.

It will of course be further appreciated that the organic residues of general formula VI above may if desired be substituted, bearing not only one or more additional reactive X-substituents but also additional preferably non-reactive substituents, the terms "reactive" and "non-reactive" here referring of course not to reactivity in the abstract but only to reactivity in the context of the reactants and reaction conditions encountered in the process of this invention.

What will be either "reactive" or "non-reactive" in that context should be normally predictable by any competent chemist, bearing in mind the nature and location of other electrophilic and/or nucleophilic substituents (if any) present upon the aromatic ring system, and prediction can be checked and empirically verified or varied by simple experiment. Nothing further need therefore be said as regards possible substitution upon the aromatic ring system; but in case it may be helpful the following additional guidance nevertheless is offered. Certain substituents may give lower yields because of their reactivity, namely those which contain acidic protons such as acyl groups, but otherwise most if not all of the commonly encountered substituents may be present without detriment, including some which might have been expected to retard the kind of nucleophilic substitution involved in the processes of this invention, such as acetamido and hydroxy groups.

Substituents which are not "non-reactive" and which would lead to poor reactions are for example nitroalkyl side chains having protons α to the nitro-group, and any side chain bearing exceptionally acidic protons (pK ≦ 12).

Substitutents which are not "non-reactive", but which would still give a clean reaction, although with concomitant reaction of the substituent are, for example, benzyl halides which would give benzyl ethers.

Under some conditions halogen substituents can effectively be "non-reactive", e.g. chloro groups in the presence of bromo groups react so much more slowly that a chloro product substituted by O—R may readily be obtained from a chlorobromo starting material.

Amino groups are a special case in that they react with the formate to give formanilides, thus deactivating the catalyst. Acylation, especially acetylation of the amine eliminates this difficulty.

As regards the substituent X in the aromatic organic compound of general formula I above which is used as starting material, it has already been indicated that X can represent bromine, chlorine or iodine; and this is believed to be correct, so long as it be understood that this statement assumes that the reaction conditions are suitably chosen to bring about the desired reaction, and that the yield will not necessarily be always satisfactory.

At the practical level of everyday chemistry, iodine-substituted aromatic organic compounds are nowadays so expensive to prepare that they tend to be encountered only in the laboratory, not in industrial preparative techniques. Hence for most purposes it can be assumed that X in the aromatic organic compound of general formula I will be either chlorine or bromine.

It has been found that in some reactions chlorine-substituted starting materials work well in the processes of this invention, especially when the chloro-group to be replaced has been suitably activated, and the relative ease and economy of introducing chlorine into the aromatic ring structure recommends the use of such a chlorine-substituted starting material wherever possible.

Nevertheless it has been found that in general the reaction will proceed most reliably, under the mildest conditions, to provide a good clean yield of the desired end-product when X is bromine. The use of such bromine-substituted starting materials is thus a very much preferred feature of this invention.

Thus, in the context of what has been said above, the compound of general formula I is preferably a compound of the formula:

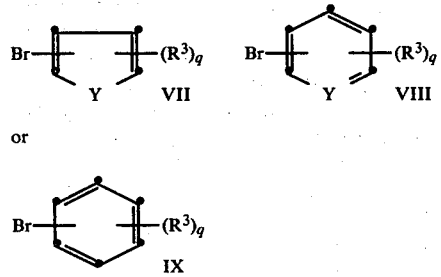

or wherein Y is oxygen, sulfur or nitrogen, q is 0, 1 or 2 and each $R^3$, which may be the same or different, is halogen, especially Cl, OH, alkoxy, aryloxy, —CHO, —CH(OMe)$_2$, —CO$_2$—alkyl, aryl, alkyl, —(CH$_2$)$_m$—alkoxy, —(CH$_2$)$_m$—halogen, especially Cl, —(CH$_2$)$_m$NHB where B is a blocking group such as an acyl group, e.g. acetyl, and m is 1, 2 or 3, or two groups $R^3$ together form a 5-, 6- or 7-membered carbocyclic or heterocyclic ring. In the aforementioned groups alkyl is preferably $C_1$- to $C_6$-alkyl, more preferably $C_1$-, $C_2$- or $C_3$-alkyl, and m is preferably 1.

Especially preferred are compounds of formulas VII and IX wherein each $R^3$, which may be the same or different, is Cl, OH, alkoxy, especially methoxy, —CH(OMe)$_2$, —CH$_2$Cl or two groups $R^3$ together form a 6-membered carbocylic or heterocyclic ring.

As regards the alcoholate of general formula II, it should first be recognized that this must bear the —O—R group which it is wished to introduce into the aromatic organic compound of general formula I in replacement for the X substituent thereon. Thus where the desired ultimate product of the synthesis is destined to bear some particular —O—R group there is little or no freedom of choice as regards the nature of the R grouping.

That being understood, the R grouping may be an unsubstituted straight- or branched-chain alkyl or cycloalkyl group with from 1 to 12 carbon atoms, an unsubstituted straight- or branched-chain alkenyl or cycloalkenyl group having one or more double bonds and with from 3 to 12 carbon atoms, an unsubstituted straight- or branched-chain alkynyl or cycloalkynyl group having one or more triple bonds and with from 3 to 12 carbon atoms, or a benzyl group; or the R grouping may be any of the aforesaid alkyl, alkenyl, alkynyl or benzyl groups bearing one or more substituents inert under the conditions of the processes of this invention. Such inert substituents should be apparent to competent chemists but it may be added, by way of example and as useful general guidance, that inert substituents which may be present include hydroxy, β-hydroxyethyloxy and alkoxycarbonyl groups, e.g. methoxycarbonyl groups. It will be understood that when R in —O—R is alkenyl or alkynyl, the oxygen atom is attached to a saturated carbon atom of the R grouping.

There are however some circumstances under which there may be an element of choice available in the selection of the R—O— grouping, and where any such freedom of choice does exist it is usually most advantageous to employ the relatively short-chain R groupings. One reason for this preference is that the previous preparation of the alcoholates proceeds with much greater ease the shorter the length of the R grouping.

Specifically, it is preferred to employ alcoholates of general formula II wherein the number of carbon atoms present in the R group does not exceed 6; preferably those wherein it does not exceed 4; and, in order of increasing preference, especially those wherein the number of carbon atoms present in the R group is 3, 2 or above all 1.

The alcoholate of general formula II used in the processes of this invention may be one wherein M represents an alkaline earth metal atom, but it is generally very much better in view of their greater reactivity to employ alcoholates wherein M represents an alkali metal atom, and above all those wherein M represents a lithium, potassium or most especially a sodium atom.

Thus in terms of reactivity, economy and indeed desirability in the final synthesis product the alcoholate of general formula II best employed will most frequently be sodium methoxide.

The reaction takes place in the liquid phase, and in fact must be performed either in solution in a suitable solvent, or under slurry conditions in a liquid medium, provided the substrate of formula I is at least partially soluble in the liquid medium. In principle any aliphatic or arylaliphatic organic alcohol can be employed as a suitable solvent or liquid medium where the alcoholate is not isolated. Where the alcoholate is isolated, other solvents or liquid media may be used alone or together with said alcoholic medium. However practical problems exist in obtaining the isolated alcoholates sufficiently free of hydroxides (which inactivate the catalyst) and of course other solvents are more expensive than for example methanol or ethanol. On the other hand in the case of butoxide or benzyloxide, the use of, for example, tetrahydrofuran may be advantageous.

It is preferred to use as the liquid medium an aliphatic alcohol of the general formula:

$$R^1-OH \qquad (III)$$

in which $R^1$ represents an optionally-substituted alkyl, alkenyl, alkynyl or benzyl group having up to 12 carbon atoms.

It is, of course, most convenient to form the alcoholate in situ, by dissolving an alkali metal or alkaline earth metal in an alcohol which is to serve as the liquid medium for the reaction; and accordingly it is much preferred that such an alcohol should be the same as that present in the alcoholate. For that and other reasons, the alcohol will most frequently be methanol. The presence of any significant amount of water will inactivate the reaction, and the reaction medium therefore must be substantially anhydrous. That requirement does not however preclude the use of commercially-available "anhydrous" grades of reactants, such as the commercially-available anhydrous grade of methanol which contains about 0.03% water.

The reaction can be successfully performed only in the presence of the formate of general formula IV. Since higher formates where $R^2$ has more than three carbon atoms could pose a purification problem, this component can most conveniently and cheaply be the formic acid ester of the same alcohol as that which serves as the reaction medium. Very frequently the formate employed will thus be methyl formate.

As presently viewed, the formate will virtually always by introduced as such, but it should not be overlooked that in principle it is possible, and sometimes it may be practical, to create the formic acid ester in situ where the reaction medium is an alcohol by introducing carbon monoxide into the reaction medium, perhaps under pressure. This consideration moreover may recommend the use of carbon monoxide as the non-oxidizing atmosphere under which the reaction should be performed.

In the case where R, $R^1$ and $R^2$ are not the same, it will be understood that the product obtained could be one in which the substituent is $OR^1$ or perhaps $OR^2$ rather than OR since the following equilibria exist:

$$[R-O]^- + R_1OH \rightleftharpoons [R_1-O]^- + ROH$$

$$[R-O]^- + R_2OCOH \rightleftharpoons [R_2-O]^- + ROCOH$$

$$R_2OCOH + R_1OH \rightleftharpoons R_2OH + R_1OCOH$$

The major substituent species present in the reaction mixture and resulting from the above equilibria will usually depend on two factors. First, the nature of R, $R^1$ and $R^2$, the group with the smaller or smallest number of carbon atoms tending to be more reactive and, secondly, the concentration of the three components.

Since it will usually be the case that the relative concentrations will be:

$$R^1OH > [R-O]_n{}^\ominus M^{n+} > > R_2OCOH$$

This means in effect that the substituent choice is between R and $R^1$ and therefore it is preferred that $R=R^1$ unless $[R^1O]_n{}^\ominus$ is much less reactive than $[RO]_n{}^\ominus$.

In general the alcoholate, the formate and the alcohol or other liquid medium may be employed in the following amounts (in moles per mole of substrate of formula I):

|  | General Range | Preferred Range |
|---|---|---|
| Alcoholate | 0.9 to 10 | 3 to 5 |
| Formate | 0.01 to 3 | 0.1 to 0.6 |
| Alcohol or other liquid medium | 1 to 100 | 10 to 40 |

The cuprous salt or salts employed as part of the catalyst system may in principle be any cuprous salt which is solubilized by the formate/alcoholate/liquid medium mixture. Specifically it has been found possible to employ cuprous chloride, cuprous sulfate, cuprous iodide, cuprous sulfite and above all cuprous bromide.

The cuprous salt(s) may and usually will be introduced into the reaction medium as such, but can if desired also be added in other forms. Thus, it is for instance possible to add cupric salt(s), e.g., cupric bromide, nd a reducing agent such as sodium sulfite so that these shall react together to form the corresponding cuprous salt(s) in situ.

In addition, curpous oxide can be added to serve as the source of curpous moiety in the reaction mixture, possibly since it displaces formic acid from the formate, and reacts therewith to create cuprous formate.

In general, the cuprous salt(s) may be employed in an amount of from 0.01 to 3 moles per mole of substrate, preferably in an amount of from 0.1 to 0.6 moles per mole of substrate.

In practicing the process of the invention, reaction conditions of time and temperature will vary depending on such factors as the nature of the X and O—R substituents, and it will be appreciated that the reaction should proceed for a time and at a temperature which will achieve substitution of the O—R substituent for the X substituent. The reaction conditions of temperature and possibly even pressure which are optimum for the reaction between any particular pair of reaction partners in the presence of any chosen catalyst system should be determined empirically. As general guidance it can however be said that present experience has shown that the reaction can always be made to proceed well at temperatures not exceeding 120° C., usually indeed at temperatures of less than 80° C., and that normal good practice requires that the reaction should whenever possible be operated at a temperature as low as is consistent with achievement of an adequate yield within an acceptable operating period and preferably at ambient pressure.

As already indicated above, the substituent most frequently to be introduced by the processes of this invention will be the methoxy group, and in that event the reactant catalyst system of choice will be sodium methoxide in the presence of methyl formate and dissolved usually in methanol. Using such a system, the reaction normally can best be conducted under reflux of the methanolic solvent, namely at about 75° C. under ambient pressures.

When the reaction is conducted under reflux of the alcoholic solvent present in the reaction mixture, the refluxing alcohol will itself create the necessary inert atmosphere so long as reflux is taking place. Before reflux has commenced it is however necessary to establish the requisite inert atmosphere by flushing out the reaction vessel with any convenient inert gas, normally nitrogen but possibly, in the circumstances envisaged above, carbon monoxide.

The process of the invention seems to be quite general in that it has not been found to fail with any reaction partners upon which it has been attempted. Its wide applicability and considerable practical value will both be appreciated from the fact that it has been employed successfully in the following commercially valuable reactions, namely:

the methoxylation of bromobenzene;
the methoxylation of 3-chlorobromobenzene;
the methoxylation of 2-bromophenol;
the methoxylation of 4-bromophenol;
the methoxylation of 2-bromoanisole;
the methoxylation of 4-bromoanisole;
the methoxylation of 6-bromo-1-acetyl-1,2,3,4-tetrahydroquinoline;
the methoxylation of 3-bromothiophene;
the methoxylation of 4-bromobenzyl bromide;
the methoxylation of 2-bromoacetophenone;
the methoxylation of 1-bromonaphthalene;
the trimethoxylation of 1,3,5-tribromobenzene;
the ethoxylation of 4-bromoanisole; and
the isopropoxylation of bromobenzene.

The process of this invention is reliable, reproducible, clean and efficient. In a few instances it has been observed that the halogen substituent X on the aromatic organic compound may to a limited extent be replaced by hydrogen rather than by the intended —O—R substituent, but experience has shown that any such side-reaction will at most take place to an extent of less than 10% and then only when a non-preferred Cu(I) source (e.g. $Cu_2O$) or solvent (e.g. t-butyl alcohol) is used. The reaction product is thus remarkably free from unwanted by-products, and remarkably clean as compared with the reaction product of classical procedures. The relatively low temperatures at which the processes according to this invention can be performed also naturally contribute to the cleanliness of the product. While one might expect aryl coupling and nucleophilic substitution by amino and hydroxyl groups present in the substrate, no such effects have so far been observed.

The mechanism of the reaction herein disclosed is not at present fully understood. It seems likely that the alcoholate, the formate or a decomposition product of the formate and the aromatic substrate of general formula I together form some kind of complex about the copper atom which so-to-speak "delivers" the R—O— substituent to the aromatic nucleus, replacing the halogen substituent X thereon.

Whatever the mechanism of the reaction, it is a fact that the reaction works well. The catalyst system employed according to this invention is essentially homogeneous, which may be contrasted with the heterogeneous systems based on copper metal used conventionally, and which no doubt accounts both for the high activity and the reliability of the process of this invention.

The only significant drawback is the high degree of sensitivity of the catalyst to oxidation. This not only means that the reaction must effectively be carried out in substantially air-free conditions, thus under a non-oxidizing atmosphere of a gas such as nitrogen, but also that it is difficult to have the catalyst system prepared in advance. While the in situ preparation of the catalyst system each time it is required does not in itself present any great problems, it makes it practically very difficult indeed to recover the catalyst system after the reaction for reuse at some future time.

This invention also extends, despite what has been said above, to a catalyst system suitable for use in the present process, namely a catalyst system which comprises a formate of general formula IV, a catalytically-effective amount of a cuprous salt and an alcoholate of general formula II, said catalyst system being substantially anhydrous and otherwise protected against oxidative breakdown. Preferably, the system is also blended with an alcohol of general formula III and/or another liquid medium as described above.

Protection against oxidative breakdown of the catalyst system can be achieved most surely by preparing, storing and using the catalyst system under an atmosphere of non-oxidizing gas or vapor, including alcohol vapor during reflux, but it can also be assisted by inclusion therein of a stabilizer.

It has been observed that, for reasons which are not understood at present, these catalyst systems are best stabilized by the presence of significant amounts of aromatic organic compounds therein.

The halogenated aromatic organic compounds of general formula I used as starting materials in the previously-described processes will serve this function as aromatic stabilizers; and indeed so too will the aromatic organic compounds of general formula V formed as end-product of those processes. Hence when the catalyst system is prepared in situ at the outset of the process and discarded at its end there is an aromatic stabilizer, of one kind or another, already present throughout the relevant period, and it is quite unnecessary then to add any additional aromatic stabilizer. Supposing however that the catalyst system is, for any reason, to be prepared before-hand and stored pending need, then it will very desirably include some suitable aromatic compound as stabilizer. The aromatic stabilizer compound is qualified as "suitable" merely to exclude the fairly-unlikely possibility that it might bear substituents which are not inert under the prevailing conditions. The inclusion of, for instance, phenol in the alcoholic or other liquid medium for the reaction is usually convenient and effective in this regard. Moreover, benzyl alcohol is likely to be an effective stabilizer in benzyloxylations.

In order that the invention may be well understood, examples will now be given to show the preparation, in more detail, but only by way of illustration, of certain useful alkoxylated aromatic compounds, as follows:

EXAMPLE 1

Methoxylation of Bromobenzene to yield Anisole

Sodium (2.3 g, 0.1 mole) was dissolved in methanol (50 ml), bromobenzene (16 g, 0.1 mole) was added, and this reaction mixture was flushed with nitrogen and heated to 50° C. Methyl formate (6 g, 0.1 mole) was then added, followed by cuprous bromide (1.4 g, 0.01 mole). The resultant pale yellow-green mixture was refluxed for 7 hours at about 70° C.

The methanol was distilled off, and dilute hydrochloric acid was added to dissolve the copper salts; the oil was extracted into ether, and thereafter separated therefrom by removal of the solvent.

The resultant pale yellow oil was submitted to GLC analysis which showed that it consisted of 56% of the desired anisole, the balance of 44% being unreacted bromobenzene.

EXAMPLE 2

Methoxylation of Bromobenzene (in the presence of Phenol) to yield Anisole

The procedure of Example 1 was repeated, but in the presence of phenol (3.8 g, 0.4 mole) which was added to the reaction mixture at the outset.

Contrary to expectation the oil recovered contained no detectable trace of diphenyl ether; but, quite unexpectedly, sampling showed upon TLC analysis that substantially 100% conversion of bromobenzene to anisole had been achieved after only 5 hours reflux.

EXAMPLE 3

Methoxylation of 3-Chlorobromobenzene to yield 3-Chloroanisole

3-Chlorobromobenzene (19.2 g, 0.1 mole) was dissolved in a solution of sodium methoxide (0.4 mole), in methanol (100 ml), and this reaction mixture was flushed with nitrogen. Methyl formate (3.6 g, 0.06 mole) was added, followed by cuprous bromide (2.9 g, 0.02 mole). The resultant suspension was refluxed for 9 hours, until the reaction was judged by TLC to be complete.

The crude reaction mixture was acidified, and extracted into isopropyl acetate. The solvent was removed by evaporation at 20° C., to give a pale yellow liquid (14.1 g; 99%), whose infra-red spectrum was identical to that of authentic 3-chloroanisole as recorded in the Aldrich catalogue. GLC analysis showed one product peak, with a higher retention time than the starting material (Bentone/OVI, 180°). GC-MS showed no detectable 3-bromoanisole and only a very small quantity of dimethylresorcinol.

EXAMPLE 4

Methoxylation of 2-Bromophenol to yield Guaiacol

2-Bromophenol (17.3 g, 0.1 mole) was dissolved in a solution of sodium methoxide (32 g, 0.6 mole) in methanol (98 ml) and this mixture was flushed with nitrogen. It should be noted that the extra equivalents of the sodium methoxide base were added in order to neutralize the phenol. Methyl formate (3.6 g, 0.06 mole) was then added, followed by cuprous bromide (2.9 g, 0.02 mole).

A vigorous reaction occurred on the addition of the cuprous bromide, and TLC showed the reaction to be virtually complete after 30 minutes.

After 1¾ hours the reaction mixture was worked up, and the product was isolated as a quantitative yield of a red oil. This was identified as guaiacol by comparison of the infra-red spectrum with an authentic specimen as recorded in the Aldrich catalogue. Bulb-to-bulb distillation of a sample yielded a colorless solid, m.p. 28° C. (lit. 28° C.).

EXAMPLE 5

Methoxylation of 4-Bromophenol to yield 4-Methoxyphenol

4-Bromophenol (7.1 g, 0.05 mole) was dissolved in a solution of sodium methoxide (0.3 mole) in methanol (60 ml), and this mixture was flushed with nitrogen. Methyl formate (1.5 g, 0.03 mole) was then added, followed by cuprous bromide (1.2 g, 0.01 mole).

This mixture was reacted under reflux at a temperature of about 70° C. After 7 hours reflux, TLC showed no appreciable traces of residual starting material.

The reaction product was worked up to give a yellow-brown oil, which crystallized slowly. Bulb-to-bulb distillation of a sample gave a colorless solid, m.p. 50°-51° C. (lit. 53°, 55° C.). Yield=5.1 g (100%) of crude material, whose infra-red spectrum is comparable with that of an authentic specimen as recorded in the Aldrich Catalogue.

EXAMPLE 6

Methoxylation of 2-Bromoanisole to yield Veratrole

2-Bromoanisole (18.7 g, 0.1 mole) was dissolved in a solution of sodium methoxide (0.4 mole) in methanol (96 ml). Then methyl formate (3.6 g, 0.06 mole) was added, followed by curpous bromide (2.9 g, 0.02 mole).

The course of the reaction was followed by TLC, which showed that it had gone to completion after about 2 hours.

After 3 hours the reaction product was worked up, in the same manner as in Example 1 except that the extraction solvent employed was isopropyl acetate. A dark liquid (12.9 g, 93%) was obtained. Its infra-red spectrum was identical to that of authentic veratrole as recorded in the Aldrich Catalogue. Bulb-to-bulb distillation was effectively quantitative, but eliminated the color to yield a colorless liquid.

EXAMPLE 7

Methoxylation of 4-Bromoanisole to yield 4-Methoxyanisole

4-Bromoanisole (18.7 g, 0.1 mole) was dissolved in a solution of sodium methoxide (0.4 mole) in methanol (96 ml), and the mixture was flushed with nitrogen. Methyl formate (3.6 g, 0.06 mole) was added thereto, followed by cuprous bromide (2.9 g, 0.02 mole).

As in Example 6 the course of the reaction was followed by TLC, which showed that it had gone to completion after 4½ hours.

The reaction product was worked up as in Example 6. On stripping off the solvent pale pink crystals (12.9 g, 93%) were obtained, m.p. 53° C. (lit 56° C.). Their infra-red spectrum proved to be identical with that of the authentic product as recorded in the Aldrich Catalogue.

EXAMPLE 8

Methoxylation of 6-Bromo-1-Acetyl-1,2,3,4-Tetrahydroquinoline with subsequent hydrolysis to yield 6-Methoxy-1,2,3,4-Tetrahydroquinoline 6-Bromo-1-acetyl-1,2,3,4-tetrahydroquinoline (23 g, 0.132 mole) was dissolved in a solution of sodium methoxide (0.528 moles) in methanol (91 ml), and the mixture flushed with nitrogen. Then methyl formate (4.8 g, 0.078 mole) was added, followed by cuprous bromide (3.9 g, 0.026 mole).

The reaction was carried out as described in Example 1, its course being followed by TLC. After 1½ hours TLC showed no starting material, and two major products which corresponded to 6-methoxy-tetrahydroquinoline and its amide. This crude product mixture was subjected to brief reflux in 20% aqueous hydrochloric acid in order to hydrolyze residual amide. Yield=17.1 g (85%) of crude 6-methoxytetrahydroquinoline; the major impurities were tetrahydroquinoline and 6-methoxyquinoline.

Distillation at reduced pressure gave an 85% recovery of the 6-methoxy-tetrahydroquinoline (b.p. 80°-100° C. at 0.2 mm) as a pale to colorless liquid. Its infra-red spectrum was identical to that of authentic material obtained by the hydrogenation of 6-methoxyquinoline. Overall yield=67%.

EXAMPLE 9

Methoxylation of 2-Bromoacetophenone to yield 2-Methoxyacetophenone

2-Bromoacetophenone (19.9 g, 0.1 mole) was dissolved in a solution of sodium methoxide formed by dissolving sodium (9.2 g, 0.4 mole) in methanol (80 ml). Then methyl formate (3.6 g, 0.06 mole) was added, followed by cuprous bromide (2.9 g, 0.02 mole).

Proceeding in the manner already described in Example 1, the course of the reaction was followed by TLC, which after 2½ hours showed the reaction to be complete.

The product was isolated by removal of solvent, taking up in dilute hydrochloric acid and extraction into isopropyl acetate. Distilling off the solvent yielded a black viscous liquid, 16.6 g. Bulb-to-bulb distillation yielded 5 g of a purified sample, the residue being polymeric; the yield was approximately 50% volatile product. Its infra-red spectrum was identical to that of the authentic material in the Aldrich Catalogue. Its NMR was as follows:

| | |
|---|---|
| CH$_3$O—Ar | 2.5 (3H) single (in CDCl$_3$) |
| CH$_3$.COAr | 3.78 (3H) single |
| H$_3$,H$_5$ aromatic | 6.7-7.0 (2H) complex |
| H$_4$,H$_6$ H's | 7.1-7.8 (2H) complex | which is consistent with the desired 2-methoxyacetophenone.

EXAMPLE 10

Methoxylation of 1-Bromonaphthalene to yield 1-Methoxynaphthalene

1-Bromonaphthalene (20.7 g, 0.1 mole) was dissolved in a solution of sodium methoxide formed by dissolving sodium (9.2 g, 0.4 mole) in methanol (100 ml), and flushing with nitrogen. Then methyl formate (3.6 g, 0.06 mole) was added, followed by cuprous bromide (2.8 g, 0.02 mole).

Proceeding in the manner described in Example 1, it was found that separation of product and starting material was not easy on TLC, so instead the reaction mixture was refluxed for what was assumed to be the maximum necessary reaction time, namely 8 hours.

The product thus obtained was isolated by removal of solvent, taking up in aqueous hydrochloric acid and extraction with isopropyl acetate. The residue after removal of the isopropyl acetate contained copper salts; filtration gave a pale brown liquid (14 g, 89%) whose infra-red spectrum was identical to that of the authentic compound as recorded in the Aldrich Catalogue. The purity by normalized GLC was >98.5%, with <0.2% starting material.

EXAMPLE 11

Trimethoxylation of 1,3,5-Tribromobenzene to yield 1,3,5-Trimethoxybenzene 1,3,5-Tribromobenzene (100 g, 0.32 moles) was dissolved in a solution of sodium methoxide in methanol formed by dissolving sodium (44 g, 1.92 moles) in methanol (480 ml). Methyl formate (18.2 ml, 0.18 moles) then added, followed by cuprous bromide (4.35 g, 0.03 moles).

The reaction was carried out under reflux for a total of 15¼ hours, with an overnight interruption. Because of that interruption the catalyst was "re-invigorated" when reflux was recommenced, thus after 7¾ hours, by adding a further 6 ml of methyl formate followed by 1.5 g of cuprous bromide.

Working-up involved stripping off the methanol, neutralization with dilute sulfuric acid and extraction into toluene. The organic extract was distilled at 0.2 mm, and a pale yellow product was obtained: 42.9 g main fraction (80.5%).

GLC analysis showed 97% of the desired product, and 2% of dimethoxy-monobromobenzene, m.p. 48.5°-49.5° C. Recrystallization from hexane gave a white solid, m.p. 50°-51.5° C. (lit. 51°-53° C.).

EXAMPLE 12

Ethoxylation of 4-Bromoanisole to yield 4-Ethoxyanisole

4-Bromoanisole (18.7 g, 0.1 mole) was dissolved in an ethanolic solution of sodium ethoxide prepared by dissolving sodium (9.2 g, 0.4 mole) in ethanol (150 ml). This solution was flushed with nitrogen, then methyl formate (3.6 g, 0.06 mole) was added, followed by acetonitrile (20 g, 0.5 mole) and cuprous bromide (2.9 g, 0.02 mole).

The reaction was performed as described in Example 1, the acetonitrile being added just prior to the cuprous bromide. Reflux for 14 hours effected almost complete conversion.

The product obtained after reflux was worked up in a manner rather different from that described in Example 1; after distilling off the ethanol, the residue was acidified and then steam distilled, yielding a pearly white product co-condensed with the water.

Filtration and drying yielded 10.8 g (70%) of 4-ethoxyanisole. A further 1.5 g (10%) was recovered from the water layer by ether extraction, m.p. 30°-31° C. After recrystallization from hexane, m.p. 34°-35° C. (lit. 38°-39° C.).

The infra-red spectrum of this product was clean and showed the expected features; but an authentic infra-red spectrum was not available for comparison.

NMR Spectrum
(run in CDCl$_3$) chemical shifts ($\delta$)

| Assignment | |
|---|---|
| 4-Ethoxy group, $\beta$ carbon: | 1.35 (trp, J = 7Hz) 3H |
| 1-Methoxy group: | 3.70 (s) |
| 4-Ethoxy group, $\alpha$ carbon: | 3.95 (qrt, J = 7Hz) 2H |

| | |
|---|---|
| -continued | |
| 2,3,5,6-Hydrogen: | 6.73 (AB db-s) 4H |

EXAMPLE 13

Isopropoxylation of Bromobenzene to yield Isopropoxybenzene

Bromobenzene (16 g, 0.1 mole) was dissolved in a solution of sodium isopropoxide in isopropanol formed by dissolving sodium (9.2 g, 0.4 mole) in isopropanol (200 ml) and then distilling off 85 ml thereof to leave 115 ml. The resultant solution was flushed with nitrogen, and then methyl formate (3.6 g, 0.06 mole) and cuprous bromide (2.9 g, 0.02 mole) were added.

This reaction mixture was refluxed for 9½ hours.

The product was then worked up in the manner described in Example 1, and a dark liquid was thus obtained. Examination by TLC indicated two components, and GLC showed that about 15% of the desired isopropoxybenzene had been formed, the rest being unchanged bromobenzene. The infra-red spectrum of the crude product showed appropriate likenesses to that of the authentic material (prepared by phase-transfer catalyzed isopropylation of phenol) but obviously was overlaid by that of bromobenzene.

EXAMPLE 14

Methoxylation of 3-Bromothiophene to yield 3-Methoxythiophene

3-Bromothiophene (16.3 g, 0.1 mole) was dissolved in a solution of sodium methoxide in methanol formed by dissolving sodium (9.2 g, 0.4 mole) in methanol (100 ml). The reaction mixture was flushed with nitrogen and methyl formate (3.6 g, 0.06 moles) then added, followed by cuprous bromide (2.9 g, 0.02 moles).

The reaction was carried out under reflux for 12 hours after which the crude product was isolated from the blue reaction mixture by filtering off insoluble material, addition of 150 ml of water and extraction into ether (3×100 ml). After removal of the solvent, two phases were left and the aqueous layer was removed by filtration through phase separation, leaving a light brown, mobile liquid (7.7 g, 68%). The infra-red spectrum of the product showed aliphatic C—H stretches below 3000 cm$^{-1}$, a characteristic thiophene ring bend at 753 cm$^{-1}$ and numerous differences from the starting material. Its NMR in CDCl$_3$ was as follows:

| 3.70 (s) 3 [H] | MeO— | H$_B$ | OMe |
|---|---|---|---|
| | | (structure) | |
| | | H$_A$  S  H$_C$ | |
| 6.06 (ddb, J = 3, 1.5) [H] | H$_C$ | | |
| 6.62 (ddb, J = 6, 1.5) [H] | H$_A$ | | |
| 7.04 (ddb, J = 6, 3) [H] | H$_B$ | | | which is consistent with it being 3-methoxythiophene.

EXAMPLE 15

Methoxylation of 4-Bromobenzyl Bromide

Sodium (10.5 g, 0.45 mole) was dissolved in 120 ml of methanol and the reaction flask flushed with nitrogen. 4-Bromobenzyl bromide (25 g, 0.1 mole) was added in a number of discrete portions. A white precipitate of sodium bromide was formed. Methyl formate (3.6 g, 0.06 mole) and cuprous bromide (2.9 g, 0.02 mole) were then added sequentially, after bringing the temperature to 60° C., and finally the reaction was refluxed for two and a half hours when the reaction was complete. After removal of the methanol, the residue was diluted with 100 ml of water and extracted into 3×70 ml of ether. After removal of the ether (to which toluene was added to azeotrope off water), a yellow liquid was left, 14.9 g (98%). Its IR Spectrum was identical to that of anisyl methyl ether prepared from anisyl alcohol.

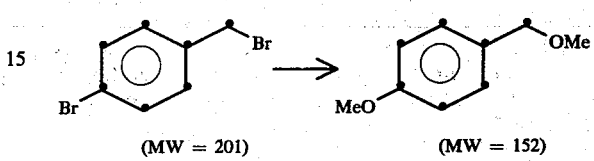

(MW = 201)   (MW = 152)

A similar yield was obtained starting from 4-bromobenzyl chloride.

EXAMPLE 16

Preparation of Syringaldehyde from 5-Bromovanillin

5-Bromovanillin (550 g, 2.38 moles) was charged to a 2 liter flask and trimethylorthoformate (330 g, 3.11 moles) and methanol (1200 ml) were added thereto. The reaction mixture was stirred and the thus-formed suspension warmed to 50° C. when 10 drops of conc. HCl were added. A solution of the acetal of 5-bromovanillin formed over a period of about 1 minute with the temperature rising to about 55° C. To prevent crystallization, the acetal solution was maintained at about 50° C. until required.

Sodium (225 g, 9.8 moles) was dissolved in methanol (1900 ml) in a 5 liter flask. The solution was cooled to 30° C. and about 20% of the already prepared acetal solution was run into the cooled solution from a heated dropping funnel. The 5 liter flask was then flushed with nitrogen and cuprous bromide (49 g, 0.34 moles) added, after which the reaction mixture was carefully brought to reflux. Foaming caused by the emission of carbon monoxide was minimized by efficient stirring, and when the reaction mixture had been at reflux for about 15 minutes the remainder of the acetal solution was carefully added over a period of about 2 hours. During that time any excessive foaming was moderated by stopping the addition. During that time also only slight heating was necessary since the reaction is an exothermic reaction.

Once the whole of the acetal solution had been added, the reaction mixture was refluxed for a further timed period of about 10 hours, and then the solution was allowed to cool to 10° C. in order to precipitate the sodium salt of syringaldehyde. The solid product was filtered, sucked dry (with the filtrate being retained) and washed with four portions of cold methanol (4×120 ml).

The crude salt was returned to the 5 liter flask, suspended in water (1500 ml) and warmed to 50° C. Conc. HCl (370 ml) was run into the suspension which quickly dissolved and then deposited yellow crystals of syringaldehyde as the solution cooled. After stirring at about 50° C. for about one hour, the crude syringaldehyde was filtered off, sucked dry, washed with water and dried at about 60° C. The yield was 360 g (83%).

The liquors were recycled once, less sodium (100 g) being needed to achieve the original sodium methoxide concentration and a greater recovery was obtained since the liquors were saturated with sodium syringaldehyde salt. The recycled liquors gave 429 g of product and thus the overall preparation afforded a total yield of 789 g of product, which is about 91% of theory. The melting point of the syringaldehyde obtained was 111° to 112° C.

An analysis by gas layer chromatography showed contamination by only 0.1% of bromovanillin and 0.02% of vanillin.

EXAMPLE 17

Methoxylation of 6-Bromo-1-Acetyl-1,2,3,4-Tetrahydroquinoline with subsequent hydrolysis to yield 6-Methoxy-1,2,3,4-Tetrahydroquinoline Hydrochloride 6-Bromo-1-acetyl-1,2,3,4-tetrahydroquinoline (112 g, 0.44 mole) was dissolved in a solution of sodium methoxide in methanol prepared by dissolving sodium (49 g, 2.13 moles) in methanol (500 ml). The solution was warmed to 45° to 50° C. and methyl formate (19.2 g, 0.32 moles) was added over 3 minutes, followed by cuprous bromide (15.2 g, 0.11 mole). The reaction temperature was then raised to 80° C. (reflux) and held there for 3 hours. Water (50 ml) was added at the end of this period and reflux continued for a further 2 hours.

Then the methanol solvent was removed at reduced pressure and the residue diluted with water (1000 ml) and isopropyl acetate (200 ml). After removal of a small amount of precipitate by filtration, the organic layer was separated and the aqueous layer extracted with isopropyl acetate (2×200 ml). The isopropyl acetate solvent was removed from the combined organic layers by evaporation under vacuum, giving crude 6-methoxy-1,2,3,4-tetrahydroquinoline (85.8 g).

The crude product was dissolved in isopropanol (210 ml) and treated with 16% w/w hydrogen chloride in isopropanol (125 ml). On cooling the hydrochloride salt crystallized out. Filtration and drying gave pure 6-methoxy-1,2,3,4-tetrahydroquinoline hydrochloride, m.p. 150° to 152° C. (yield 66 g; 75% of theory).

What is claimed is:

1. A catalyst for use in a process for substituting for a halogen atom attached to the nuclear carbon atom of an aromatic ring, wherein the halogen-substituted aromatic ring comprises the whole or part of a partially or wholly aromatic substrate selected from the group consisting of a monocyclic carbocyclic compound, a polycyclic carbocyclic compound, a monocyclic heterocyclic compound and a polycyclic heterocyclic compound; a substituent of the formula —O—R, wherein R represents a substituent selected from the group consisting of alkyl having from 1 to 12 carbon atoms, alkenyl having from 3 to 12 carbon atoms, alkynyl having from 3 to 12 carbon atoms and benzyl; which process comprises reacting said substrate with an alcoholate of the formula:

$$M^{n+}[O-R]_n^{\ominus}$$

wherein M represents an alkali metal atom or an alkaline earth metal atom; n is the valency of M, and R is as defined above, in the presence of a catalytically-effective amount of said catalyst; which catalyst comprises a mixture of a formic acid ester of an organic alcohol having the formula $$R^2-O-CO-H$$

wherein $R^2$ represents a substituent selected from the group consisting of alkyl having from 1 to 12 carbon atoms, alkenyl having from 3 to 12 carbon atoms, alkynyl having from 3 to 12 carbon atoms and benzyl; and a cuprous salt; said catalyst being substantially anhydrous and protected against oxidative breakdown.

2. A catalyst according to claim 1 which additionally comprises a liquid medium.

3. A catalyst according to claim 2 wherein the liquid medium is an alcohol of formula $$R^1OH$$

wherein $R^1$ is selected from the group consisting of alkyl having from 1 to 12 carbon atoms, alkenyl having from 3 to 12 carbon atoms, alkynyl having from 3 to 12 carbon atoms and benzyl.

4. A catalyst according to claim 1 wherein the catalyst is protected against oxidative breakdown by maintaining the catalyst under an atmosphere of a non-oxidizing gas.

5. A catalyst according to claim 1 wherein the molar ratio of the formic acid ester to the cuprous salt is from about 0.01:3 to 3:0.01.

6. A catalyst according to claim 5 wherein the molar ratio of the formic acid ester to the cuprous salt is from about 0.1:0.6 to 0.6:0.1.

7. A catalyst according to claim 1 wherein the cuprous salt is selected from the group consisting of cuprous bromide, cuprous chloride, cuprous iodide, cuprous sulfate and cuprous sulfite.

8. A catalyst according to claim 7 wherein the cuprous salt is cuprous bromide.

* * * * *